(12) United States Patent
Begum

(10) Patent No.: US 6,758,215 B2
(45) Date of Patent: Jul. 6, 2004

(54) AROMATIC TRAVEL MASK

(76) Inventor: Paul G. Begum, P.O. Box 58045, Salt Lake City, UT (US) 84158

( * ) Notice: Subject to any disclaimer, the term of this patent is extended or adjusted under 35 U.S.C. 154(b) by 0 days.

(21) Appl. No.: 10/273,031

(22) Filed: Oct. 17, 2002

(65) Prior Publication Data

US 2004/0074498 A1 Apr. 22, 2004

(51) Int. Cl.$^7$ ............................................. A61M 16/00
(52) U.S. Cl. .......................... 128/203.29; 128/204.13; 128/202.15
(58) Field of Search ...................... 128/203.29, 204.13, 128/206.19, 863, 201.13, 202.15; 2/15

(56) References Cited

U.S. PATENT DOCUMENTS

| | | | | |
|---|---|---|---|---|
| 127,331 A | * | 5/1872 | Flora | 128/203.29 |
| 145,337 A | * | 12/1873 | Crofutt | 128/206.19 |
| 152,215 A | * | 6/1874 | Crofutt | 128/206.19 |
| 301,111 A | * | 7/1884 | Genese | 128/203.29 |
| 505,653 A | | 9/1893 | Gumeson | |
| 831,623 A | * | 9/1906 | Murphy | 128/203.29 |
| 1,224,039 A | | 4/1917 | Synohubyk | |
| 1,275,127 A | * | 8/1918 | Campbell | 2/15 |
| 1,366,437 A | * | 1/1921 | Wagenhorst | 128/202.15 |
| 1,807,475 A | | 5/1931 | Gibson | |
| 2,023,267 A | * | 12/1935 | De Saint Rapt et al. | 128/202.15 |
| 2,056,753 A | * | 10/1936 | Wagner | 128/206.19 |
| 2,342,840 A | * | 2/1944 | Cadous | 604/308 |
| 2,537,768 A | * | 1/1951 | Laporte | 2/15 |
| 2,942,270 A | * | 6/1960 | Enriant | 2/15 |
| 3,067,425 A | * | 12/1962 | Colley | 2/6.2 |
| 3,699,958 A | * | 10/1972 | Szucs | 604/304 |
| 4,122,847 A | * | 10/1978 | Craig | 128/858 |
| 4,271,834 A | * | 6/1981 | Tanaka | 128/205.27 |
| 4,467,799 A | * | 8/1984 | Steinberg | 128/206.14 |
| 4,488,547 A | | 12/1984 | Mason | |
| 4,503,851 A | * | 3/1985 | Braunroth | 128/203.29 |
| D293,829 S | | 1/1988 | Johnson | |
| 4,790,307 A | * | 12/1988 | Haber et al. | 128/206.19 |
| 4,797,956 A | * | 1/1989 | Boyce | 2/431 |
| 4,856,509 A | * | 8/1989 | Lemelson | 128/206.19 |
| 4,872,217 A | * | 10/1989 | Kitayama | 2/15 |
| 4,912,777 A | | 4/1990 | Gasbarro | |
| 4,944,294 A | * | 7/1990 | Borek, Jr. | 128/206.19 |
| 4,969,473 A | * | 11/1990 | Bothwell | 128/858 |
| 5,007,114 A | | 4/1991 | Numano | |
| 5,010,594 A | | 4/1991 | Suzuki | |
| 5,020,533 A | * | 6/1991 | Hubbard et al. | 128/206.23 |
| 5,067,174 A | * | 11/1991 | Ritchey et al. | 2/10 |
| 5,357,947 A | * | 10/1994 | Adler | 128/201.13 |
| D368,960 S | | 4/1996 | Lanford | |
| 5,538,013 A | * | 7/1996 | Brannon | 128/857 |
| 5,940,886 A | * | 8/1999 | McCarthy Smith | 2/206 |
| D421,117 S | | 2/2000 | Hunter | |
| 6,070,578 A | * | 6/2000 | Baughman et al. | 128/205.27 |
| 6,375,724 B1 | | 4/2002 | Foti | |
| 6,382,213 B1 | | 5/2002 | Sanpei | |
| 6,412,486 B1 | | 7/2002 | Glass | |
| D465,234 S | | 11/2002 | Gordon | |
| 6,550,474 B1 | * | 4/2003 | Anderson et al. | 128/200.24 |

* cited by examiner

Primary Examiner—Aaron J. Lewis

(57) ABSTRACT

An aromatic travel mask that fits over the nose and mouth area of a wearer's face for filtration of air, particularly recycled air in the travel compartment of a common carrier, the travel mask having a face shield with an aroma patch that emits a pleasant aroma and a retainer such as a head band for retaining the face shield against a user's head, the retainer having slidable ear plugs for blocking noise. The face shield also has foldable eye flaps for blocking light when the flaps are extended, the flaps preferably having thermal gel packs for cooling or warming the eye lid area during use.

19 Claims, 3 Drawing Sheets

AROMATIC TRAVEL MASK

BACKGROUND OF THE INVENTION

This invention relates to an aromatic travel mask, and in particular to a disposable air filtration mask that includes a small activatable aromatic packet and comfort accessories including earplugs and an eye flap for use during napping.

This invention provides a solution for the concern of many modern travelers who travel by airplane, ship, bus or train in a closed environment with recycled air. In addition to the normal closed quarters of the modern travel environment, many carriers are closely regulating the quantity of fresh outside air that is mixed with recirculated air in the passenger compartment.

Use of recirculate air is particularly prevalent in air travel where added external air is typically extracted from engine compressors thereby reducing the efficiency of the engine and increasing the fuel costs and ultimate costs in travel. The cost effectiveness of utilizing recirculated air in ship, train and bus travel is also an important consideration, particularly when the outside air is either cold or hot thereby requiring heating or cooling before the new change of air is circulated.

The use of the invented aromatic travel mask ensures that a passenger is reasonably protected from inhaling microbes, pollens and allergens. In addition, for many travelers, the journey is best spent dozing or sleeping. The use of a disposable travel mask having a small aroma packet to infuse the mask with a pleasant aroma transforms the experience of wearing a filtration mask into one that is positive and beneficial. The aroma packet that is attached inside of the mask near the nose area and can be activated at the time of using the mask to ensure a fresh aroma that has not faded while the masks have been stored. The addition of earplugs incorporated on the headband of the aroma mask enables the wearer to isolate themselves from the noise of the travel compartment and enjoy a serene doze or nap. Additionally, to aid in napping, the aroma mask is preferably provided with an eye flap that can be positioned to block light to the eyes and improve the opportunity for sleep or isolation from the cabin environment. The mask is preferably provided with markings which may be in the form of amusing characters, advertising or slogans and the like to encourage use of the aromatic travel mask.

It is a primary object of this invention to provide a filtration mask that can reduce or eliminate the inhalation of possible detrimental microbes, pollens and allergens when traveling on a common carrier.

It is also an object of this invention that the filtration mask be disposable and equipped with a small aroma packet to provide herbal aroma therapy or simply a pleasant smell while wearing the mask.

Furthermore, it is an object of this invention to include a headband for maintaining the mask in position wherein the headband includes slidable or adjustable earplugs for suppressing noise.

In addition, it is an object of this invention to include a contoured and moldable eye flap that can be placed in position covering the eyes while wearing the filtration mask to suppress light and aid in napping.

Also, it is an object of this invention to include markings on the mask that promote use of the mask.

These and other objects of the invention will be disclosed in greater detail in the summary of the invention and in the detailed description of the preferred embodiments of the invention.

SUMMARY OF THE INVENTION

This invention relates to an air filtration mask having an aroma emitting area to provide a pleasant aroma to the wearer of the mask, particularly a traveler on a common carrier. The aromatic travel mask of this invention includes a number of features for the comfort and pleasure of the traveler including adjustable earplugs to block noise and eye flaps to block light, allowing a travel passenger to nap or doze while breathing filtered air that is enhanced with a pleasant aroma.

The aromatic mask has an air-filtration face shield that is constructed and configured to cover the nose and mouth area of a wearer's face allowing the wearer to breathe filtered air. The aromatic mask has a retainer connected to the face shield to securely hold the face shield against the wearer's face during use. The retainer is typically elastic with either an elastic headband around the back of the user's head for formed respirator-type masks, or elastic or string-like ear loops for surgical-type masks.

The face shield has an aroma emitting area that is preferably located between the nose and mouth area of a wearer when wearing the mask. It is understood that the entire face shield can be impregnated with an aroma generating substance. However, because other passengers may be affected by the aroma, it is preferred that the aroma generating substance be a central patch on the inside of the face shield which is practical and cost effective.

In addition to the aroma patch, the aromatic travel mask of this invention preferably includes other features for the comfort and pleasure of the wearer. Attached to the retainer are adjustable earplugs that are used by the wearer to block noise. Also, attached to the face shield is a light blocking flap that is folded against the inside of the face shield. The eye flap or flaps may be raised by the wearer to block light allowing the traveler to nap or doze while enjoying the aromatic mask. The eye flaps preferably include thermal gel packs that can be heated or chilled and inserted into a flap pocket for soothing the eye lid area of the wearer.

Additionally, the face shield of the mask is preferably imprinted with markings in the form of amusing or informative graphics and may include a straw hole to allow the wearer to drink while wearing the mask.

Also, the mask is preferably provided in different colors that may suggest the aroma, for example, yellow for lemon, green for mint, pink for cherry or raspberry, and the like.

These and other features are described in greater detail with reference to the drawings in the detailed description of the preferred embodiments of this invention.

DETAILED DESCRIPTION OF THE PREFERRED EMBODIMENTS

Figure 1:
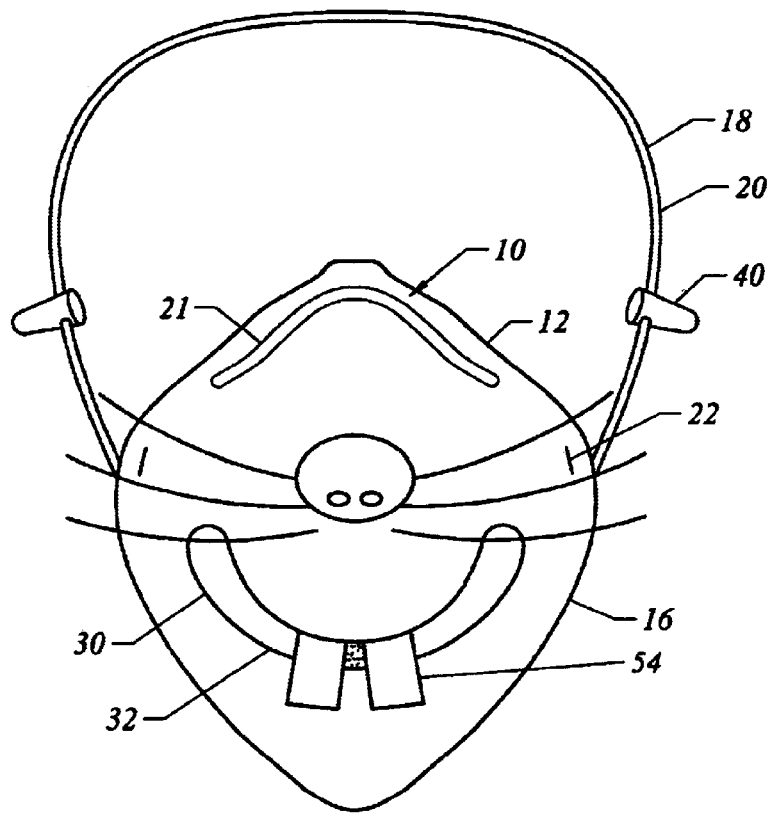
FIG. 1 is a front perspective view of one embodiment of the aromatic travel mask of this invention.
Figure 2:
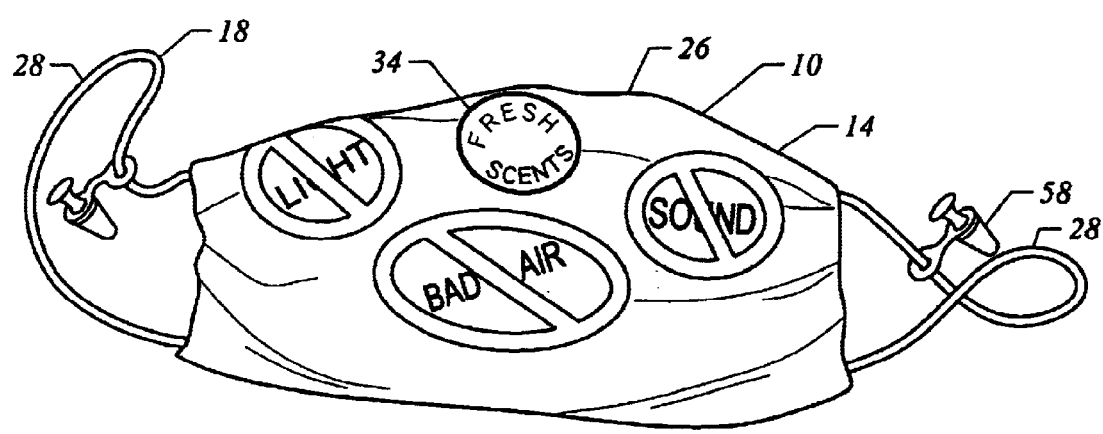
FIG. 2 is a front perspective view of another embodiment of the aromatic travel mask of this invention.

The aromatic travel mask of this invention is designated generally by the reference numeral 10. Although the form of the aromatic travel mask can vary, it is typically a formed particulate respirator mask 12 as shown in FIG. 1, or a cloth-like surgical mask 14 as shown in FIG. 2. Both embodiments of the mask 10 perform the common basic task of air filtration to remove dust, dander and most airborne pollens, allergens and microbes.

Referring to the embodiment of the aromatic travel mask 10 of FIG. 1, the respirator-type mask 12 includes a pliable, but form-retaining face shield 16 and a retainer 18 in the form of an elastic strap 20 connected to the face shield 16 by staples 22. To aid in conforming the face shield 16 to the wearer's face, a deformable metal reinforcement strip 24 is located on the outside of the face shield 16 at the bridge of the wearer's nose. When the mask is positioned on a wearer's face, the strip 24 can be bent by finger pressure to conform the mask to the contours of the wearer's face and prevent leakage during use.

In contrast, the aromatic travel mask 10 of FIG. 2 has a face shield 26 that is fabricated of a flexible, cloth-like material that conforms to the wearer's face by action of the head retainer 18. In FIG. 2 the head retainer 18 is in the form of elastic loops 28. The loops 28 are installed around a wearer's ears, thereby spreading the mask over the user's face to cover both mouth and nose.

Both masks 12 and 14 include markings 30. In FIG. 1 the markings 30 are in the form of graphics 32 of an amusing animal-like character and in FIG. 2 the markings 30 are in the form of informational symbols 34. It is to be understood that other types of markings may be used including instructional material on how to use the mask, advertisements or branding logos for promoting the travel carrier or a sponsor of the mask.

Figure 3:
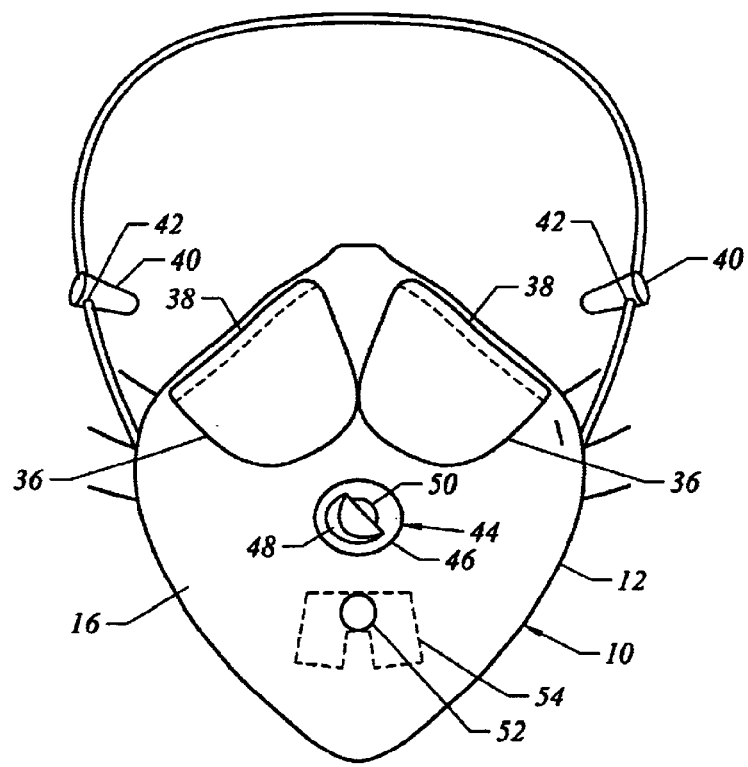
FIG. 3 is a back perspective view of the travel mask of FIG. 1.
Figure 4:
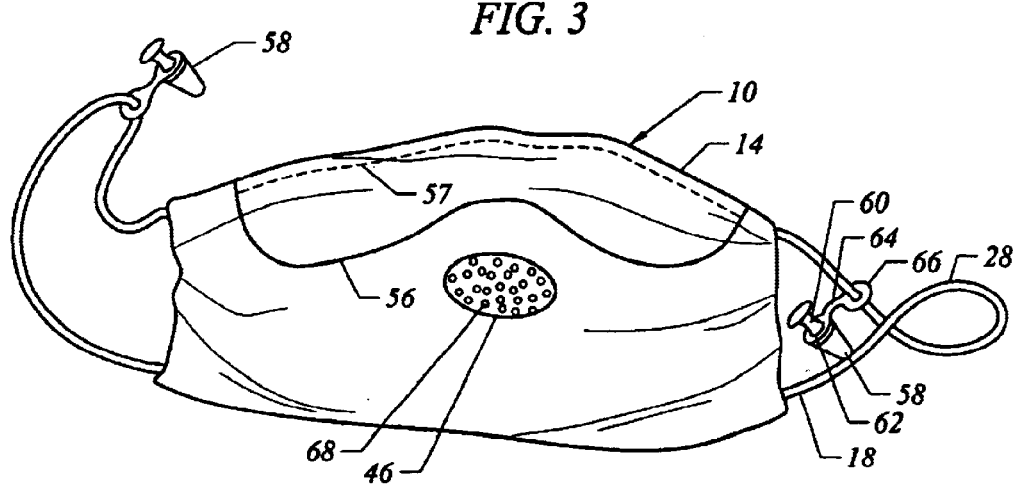
FIG. 4 is a back perspective view of the travel mask of FIG. 2.

Referring to FIGS. 3 and 4, the backside of the masks 12 and 14 are shown to illustrate important features incorporated into the mask 10 for the comfort and convenience of the traveler. The formed respirator mask 12 of FIG. 1 includes a pair of eye flaps 36 which are connected to the face shield 16 by folds 38 along the edge of the face shield. The eye flaps 36 are formed of a soft, pliable, light blocking material. The eye flaps 36 can be raised along the folds 38 to cover a wearer's eyes for use during dozing or napping.

Figure 7:
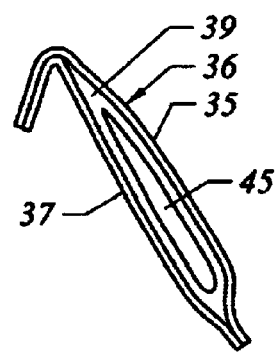
FIG. 7 is a partial cross-sectional view of the eye flap of FIG. 6 showing an internal thermal gel pack.

As shown in FIG. 7, the construction of the eye flaps 36 is preferably in layers with an outer layer 35 and an inner layer 37 to provide a pocket 39 for inclusion of a thermal gel pack 45. The gel pack 45 may be separately heated or cooled at the desire of the wearer and inserted into the pocket 39 during use or, alternately, the entire mask with the pre-installed gel pack can be thermally treated before use. The gel pack is designed to provide relief from headache or simply to provide an added pleasurable experience when wearing the mask.

Additionally, a pair of soft foam earplugs 40 are provided. The earplugs 40 have a hole 42 through the plugs through which the elastic strap 20 is threaded to enable the earplugs 40 to pivot and slide along the strap for placement in a wearer's ears to block noise. In this manner, the plugs 40 and elastic strap 20 can be adjusted and positioned for the comfort of a particular wearer.

At the center of the face shield 16, at a location between the nose and the mouth of a traveler wearing the mask, is an aroma patch 44. In FIG. 3, the aroma patch 44 is in the form of an aroma packet 46 with a peel-off seal 48, shown partially removed to expose an aroma source 50. The aroma source 50 may be in the form of an absorbent material impregnated with an oil of a pleasing or therapeutic aroma emitting substance. The aroma emitting substance preferably has therapeutic effects such as camphor or eucalyptus, but may simply be pleasing in as the scent of mint or lemon.

Finally, for the formed mask 12 in particular, a hole 52 is provided for the insertion of a straw to enable the wearer to drink while wearing the mask. The hole 52 is protected by a flap 54 (shown in dotted line). The flap 54, as illustrated in the embodiment of FIG. 1, is incorporated into the graphics for the amusement of the wearer, particularly a traveling child. It is to be understood that a plain flap mounted on the front side of the mask may be used. The air flap 54 will normally block air from entering through the hole 52 when a user is wearing the mask and is not using a drinking straw.

Referring now to FIG. 4, the aromatic travel mask 10 in the form of the surgical mask 14 has a single, contoured eye flap 56 fabricated from a light blocking material. The eye flap 56 is pliable with a fold 57 to allow the wearer to adjust the eye flap 56 across the eyes to block light. As noted, the eye flap 56 can include a thermal gel pack 45 as shown in FIG. 7.

Additionally, the cloth-like surgical mask 14 has a pair of earplugs 58 formed of a rubber-like material with a constricted portion 60 around which a loop 62 of a tether 64 is engaged. A loop 66 at the opposite end of the tether 64 loops around the elastic ear loops 28 that form the head retainer 18. In this manner the earplugs 58 can slide along the elastic loops 28 and be located at the wearer's ears for the comfort of the traveler. In addition, the face shield 26 of the mask 14 includes an aroma patch 46. The aroma patch 46 in FIG. 4 is in the form of a microsphere splotch 68. When the microsphere splotch 68 is scratched, microspheres containing an aromatic substance are broken open releasing a desired aroma. As noted, the aroma can be therapeutic or simply pleasant to the wearer of the mask.

Figure 5:
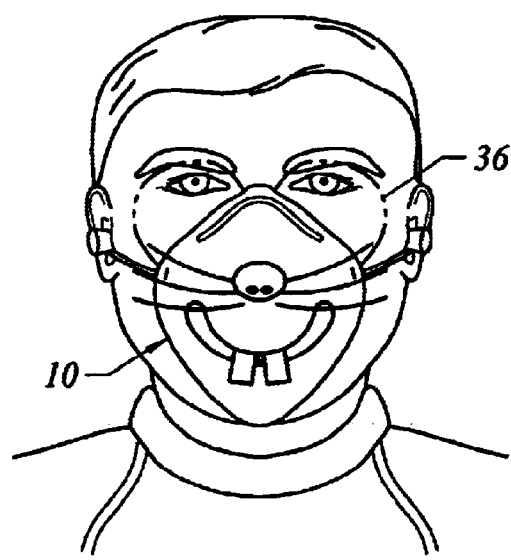
FIG. 5 is a front perspective view of the mask of FIG. 1 covering the nose and mouth area of a wearer.
Figure 6:
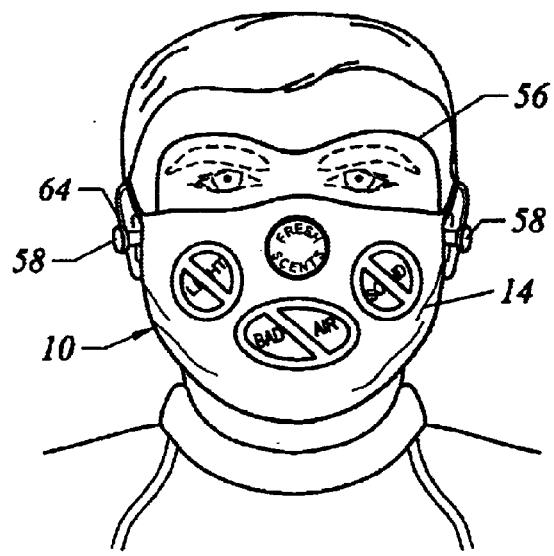
FIG. 6 is a front perspective view of the mask of FIG. 2 covering the nose and mouth area of a wearer with an eye flap extended to cover the wearer's eyes.

Referring now to FIGS. 5 and 6, the manner of wearing the aromatic travel mask is illustrated. In FIG. 5, the traveler has the formed respirator mask 12 comfortably positioned over nose and mouth with the elastic strap 20 positioned across the ears with the earplugs 40 partially inserted in the traveler's ears to block sound. The traveler in FIG. 5 is not utilizing the eye flaps 36 which would extend to cover the wearer's eyes as shown in phantom.

Similarly, the traveler in FIG. 6 has the cloth-like surgical mask 14 installed over the wearer's lower face with the eye flap 56 folded upward to block light from the user's eyes, as shown in dotted line. The earplugs 58 on the tethers 64 are shown inserted into the traveler's ears for blocking noise. For the full benefit of the aromatic travel masks 10 the wearer in each figure has activated the aroma patch (not visible). In this manner the traveler may enjoy all attributes of the aromatic travel mask of this invention.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An aromatic mask that fits over a nose and mouth area of a wearer's face and that includes an optional eye shade that can be raised to cover a wearer's eyes comprising:

an air-filtration face shield constructed and configured to cover the nose and mouth area of a wearer's face allowing the wearer to breathe filtered air through the face shield, a retainer connected to the face shield and arrangeable on a wearer's head with the face shield retained against the wearer's face, wherein at least part of the face shield has an area emitting a pleasant aroma that the wearer breathes when the mask is worn and the face shield is retained against the wearer's face, wherein the face shield has at least one light blocking flap connected to the face shield, and wherein when the mask is worn the light blocking flap is moveable from a first position against the face shield to a second extended position covering the wearer's eyes.

2. The aromatic mask of claim 1 wherein the part of the face shield having the pleasant aroma emitting area is located between the nose and mouth area of a wearer when wearing the mask.

3. The aromatic mask of claim 2 wherein the part of the face shield having the pleasant aroma emitting area comprises an aroma patch.

4. The aromatic mask of claim 3 wherein the aroma patch is activatable by the wearer to emit a pleasant aroma.

5. The aromatic mask of claim 3 wherein the aroma patch comprises an aroma packet having a peel-off seal.

6. The aromatic mask of claim 3 wherein the aroma patch comprises a splotch of microspheres containing an aromatic substance.

7. The aroma mask of claim 1 wherein the retainer has noise blocking earplugs positionable at a wearer's ears for insertion into the ears of the wearer to block noise.

8. The aroma mask of claim 7 wherein the noise blocking earplugs are slidabley connected to the retainer.

9. The aromatic mask of claim 7 wherein the retainer includes an elastic head band and the earplugs are connected to the elastic head band.

10. The aromatic mask of claim 7 wherein the earplugs have a tether and the tether connects the earplugs to the retainer.

11. The aromatic mask of claim 10 wherein the retainer includes ear loops and the ear loops are installed around a wearer's ears when the mask is worn.

12. The aroma mask of claim 1 wherein the light blocking flap is foldable against the face shield when not in use by a wearer of the mask.

13. The aroma mask of claim 1 wherein the retainer has noise blocking earplugs positionable at a wearer's ears for insertion into the ears of the wearer to block noise.

14. The aromatic mask of claim 1 wherein the face shield has a straw hole, and a flap covering the straw hole wherein the straw hole is located proximate to a wearer's mouth when the mask is worn.

15. The aromatic mask of claim 1 wherein the face shield includes graphics.

16. The aromatic mask of claim 1 wherein the face shield is a formed particulate respirator with two foldable light blocking flaps.

17. The aromatic mask of claim 16 wherein the foldable light blocking flaps contain a thermal gel pack.

18. The aromatic mask of claim 1 wherein the face shield is fabricated of a cloth-like material with a single, foldable, light blocking flap.

19. The aromatic mask of claim 18 wherein the foldable light blocking flap contains a thermal gel pack.

* * * * *